US007752768B2

(12) United States Patent
Young (10) Patent No.: US 7,752,768 B2
(45) Date of Patent: Jul. 13, 2010

(54) MARKER TEMPLATE FOR BREAST REDUCTION SURGERY

(75) Inventor: Leroy Young, Wildwood, MO (US)

(73) Assignee: Bodyaesthetic Research Center, Inc., Creve Coeur, MO (US)

( * ) Notice: Subject to any disclaimer, the term of this patent is extended or adjusted under 35 U.S.C. 154(b) by 70 days.

(21) Appl. No.: 12/178,417

(22) Filed: Jul. 23, 2008

(65) Prior Publication Data
US 2010/0023122 A1    Jan. 28, 2010

(51) Int. Cl.
  *B43L 13/20*    (2006.01)
  *A61B 19/00*    (2006.01)
(52) U.S. Cl. .......................................... 33/512; 33/566
(58) Field of Classification Search ................... 33/512, 33/562, 563, 565, 566
  See application file for complete search history.

(56) References Cited

U.S. PATENT DOCUMENTS

| 2,932,296 | A | * | 4/1960 | Sanders ..................... 606/167 |
| 3,071,171 | A | * | 1/1963 | Guerrero ...................... 33/524 |
| 4,279,259 | A | * | 7/1981 | Lee et al. ..................... 600/587 |
| 4,892,096 | A | * | 1/1990 | Narayanan et al. ............. 606/1 |
| 4,944,737 | A | * | 7/1990 | Bloom ........................... 606/1 |
| 5,195,893 | A | * | 3/1993 | Casale ........................... 434/87 |
| 5,618,292 | A | * | 4/1997 | Poler ........................... 606/166 |
| 5,676,161 | A | * | 10/1997 | Breiner ....................... 128/898 |
| 2002/0143326 | A1 | * | 10/2002 | Foley et al. .................... 606/41 |
| 2003/0051362 | A1 | * | 3/2003 | Buckman et al. .............. 33/566 |
| 2003/0115767 | A1 | * | 6/2003 | Wedekind et al. ............. 33/566 |
| 2007/0104695 | A1 | | 5/2007 | Quijano et al. |
| 2007/0123915 | A1 | * | 5/2007 | Kammerer et al. .......... 606/151 |
| 2007/0141972 | A1 | | 6/2007 | Keenan |
| 2009/0163949 | A1 | * | 6/2009 | Rolnick et al. .............. 606/213 |

* cited by examiner

Primary Examiner—Christopher W Fulton
(74) Attorney, Agent, or Firm—Thompson Coburn LLP (57) ABSTRACT

A surgical incision marking template for marking a breast with an intended incision pattern prior to surgery comprises a pliable structural portion with a guide portion. The guide portion is substantially shaped and/or shapeable into a "keyhole" pattern. The keyhole pattern corresponds to the incision pattern generally utilized for the vertical short scar and the inferior pedicle techniques for breast reduction or mastopexy surgery and comprises a generally circular pattern and a generally linear pattern, with the generally linear pattern extending downward from the generally circular pattern when the template is placed on a standing patient. The pliable nature of the structural portion not only allows the shape of the guide portion to be altered but also allows the structural portion to conform to the curvature and shape of the breast. Methods of use for the template to mark the breast are also disclosed.

17 Claims, 4 Drawing Sheets

MARKER TEMPLATE FOR BREAST REDUCTION SURGERY

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates generally to the field of breast reduction and breast lift (mastopexy) surgery. In particular, the invention relates to a device for marking a pattern on a breast prior to performing surgery on the breast (typically, breast reduction surgery accompanied by nipple/areola relocation) and methods of use thereof.

Figure 1:
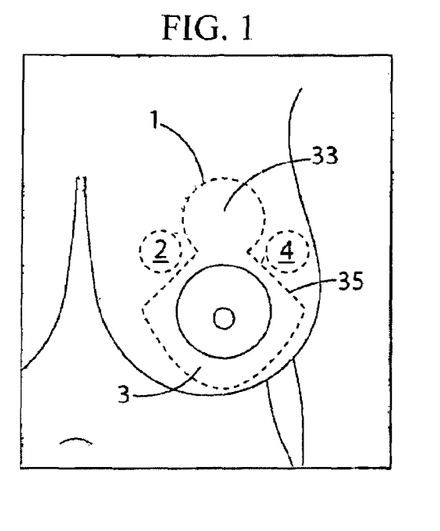
FIG. 1 is an anteroposterior view of a breast illustrating a representative incision pattern (dashed line) of the vertical short scar technique for breast reduction surgery.
Figure 2:
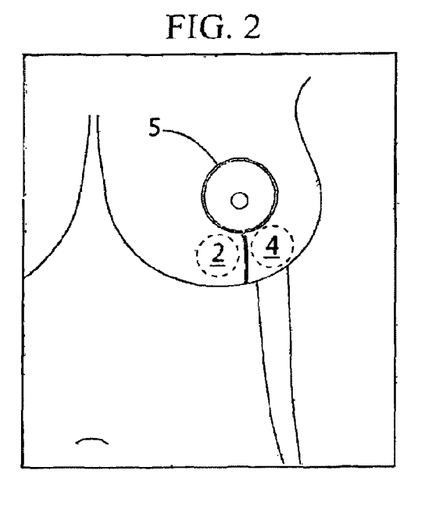
FIG. 2 is an anteroposterior view of a breast illustrating the post-operation shape and post-operative scarring (solid line) following vertical short scar breast reduction surgery.
Figure 3:
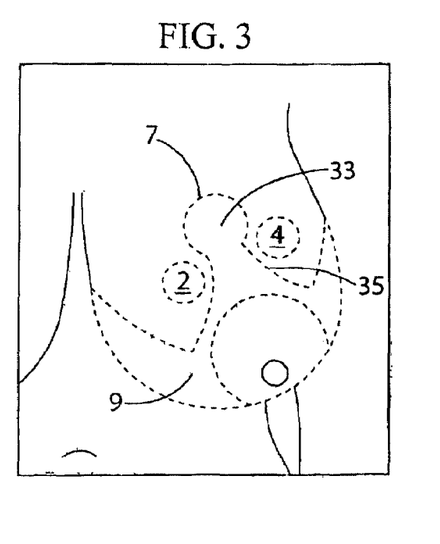
FIG. 3 is an anteroposterior view of a breast illustrating a representative incision pattern (dashed line) of the inferior pedicle technique (Wise pattern technique) for breast reduction surgery.
Figure 4:
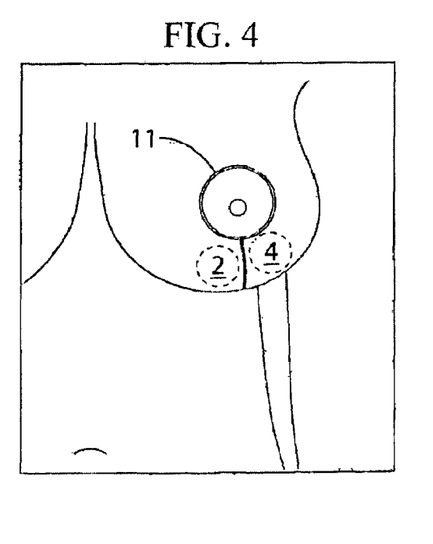
FIG. 4 is an anteroposterior view of a breast illustrating the post-operation shape and post-operative scarring (solid line) following inferior pedicle breast reduction surgery.

Two of the most commonly performed breast reduction and lift techniques are the vertical short scar technique and the inferior pedicle technique (also know as the Wise pattern reduction). The use of the vertical short scar technique is popular due to its minimal scarring and round breast shape post-surgery. This technique entails, among other things, the surgeon creating a "keyhole" or racquet-shaped pattern (also referred to as a lollipop pattern) with an incision around the areola and vertically down to the inframammary crease. FIG. 1 illustrates a general incision pattern for the vertical short scar technique indicating the incision as a dashed line 1, and the area of skin to be removed 3. The breast is reduced through removal of the lateral and inferior tissues, leaving the upper pole mostly untouched. The technique results in a scar that is proximal to the periphery of the areola and extends generally vertically to the IMC. FIG. 2 illustrates the post surgery appearance of the breast and indicates the resulting scarring as a solid line 5. For women with the largest, droopiest breasts, the inferior pedicle technique may be a better option than the vertical short scar technique. The incision accompanying this technique is in the shape of a W and removes a larger amount of tissue. FIG. 3 illustrates a general incision pattern for the inferior pedicle technique indicating the incision as a dashed line 7, and the area of skin to be removed 9. Excess glandular tissue, fat, and skin are removed and the nipple and areola are moved to a new, higher position. FIG. 4 illustrates the post surgery appearance of the breast and the resulting scarring as a solid line 11.

Typically, a surgeon marks the location(s) of the incisions prior to making such incisions during the surgery. Such marking may be made with a "permanent" marker such as a Sharpie® available from Sanford Corporation of Oakbrook, Ill. FIGS. 1-4 show two areas of a breast generally defined by the dashed lines enclosing them designated 2 and 4. As shown in FIGS. 1 and 3 depicting a breast before surgery, area 2 and area 4 are separated and above the position of the nipple and areola. As shown in FIGS. 2 and 4 depicting a breast after surgery, area 2 and area 4 are drawn together below the new position of the nipple and areola. This example illustrates how the shape of the marking must "predict" how the skin remaining after removal of the excess tissue and skin will fit together to form the post surgery shape of the breast and areola. For example, a perfectly circular marking made prior to surgery for an incision to place the areola may result in an undesirably skewed circular shaped areola post surgery. Therefore, the shape of the pre-surgery incision pattern marking(s) must take into account how the skin will be pulled together to form the post surgery shape. Markings may be made free hand (i.e., without the aid of a guide or template), however, a guide is often used. One such known type of guide is comprised of a shaped wire. Wire guides are relatively rigid and are not intended nor are they readily made to conform to the highly variable surface of a breast. As a result, utilizing such wire guides has resulted in less than optimum or even mistaken incision patterns on the surface of breasts. Therefore, a need exists for a marking device, guide, or template that, among other things, better conforms to the surface of breasts to facilitate more precise and reliably accurate incision patterns to be marked on a breast in a relatively easy and quick manner.

SUMMARY OF THE INVENTION

The present invention comprises a surgical incision marking template for marking a breast with an intended incision pattern prior to surgery. In a preferred embodiment, the template is made to include a pliable structural portion with a guide portion. The guide portion circumscribes a keyhole pattern that corresponds to the incision pattern frequently used in breast reduction surgery. The keyhole pattern comprises a generally circular pattern and a generally linear pattern. The pliable structure is preferably made of an elastomer such as for example, but not limited to, silicone, rubber, or polytetrafluoroethylene (PTFE). The pliable nature of the structural portion allows for the shape of the template to be readily altered by the surgeon, thus varying the shape of the keyhole pattern of the guide portion, such as for example by widening the generally linear portion of the keyhole pattern. Yet another advantage of the present invention is that the pliable nature of the template allows it to closely conform to breasts of different sizes and shapes, thereby minimizing the number of such templates a surgeon may need to accommodate his patient population. This reduces his investment in inventory required for his/her practice.

The present invention also includes a method for marking a breast with an incision pattern for breast reduction surgery using the template. In a preferred embodiment, the method comprises placing the template device on a breast such that the top edge of a circular pattern of the guide portion is at the level of the desired post-surgery position of the top edge of the areola. Once placed at the desired level, the template may be secured, such as by taping, into place. The overall shape of the template may then be adjusted so that the guide portion forms a keyhole pattern corresponding to the desired incision pattern. The incision pattern may then be readily and accurately marked onto the breast by tracing along one or more edges of the guide portion. Symmetry between a patient's breasts may be maintained by measuring a distance from a suprasternal notch of a patient to a location at or about the desired post-surgery position of the top edge of the areola. That location is then used to determine the positioning of the template device and to ensure that the post-surgery position of the areolas is symmetrical, near symmetrical, or as near symmetrical as is reasonably achievable.

DETAILED DESCRIPTION OF THE PREFERRED EMBODIMENT

The present invention in its preferred embodiment is directed to a pliable template and methods for marking the incision pattern for breast reduction or lift surgery. The invention preferably comprises a template formed, at least in part, of a material that may be readily and accurately made to conform to the surface of a breast by a surgeon prior to surgery. The template comprises a guide portion having edges that define the guide for marking the incision pattern on a breast.

A. Template Material

The template is preferably comprised of a material that is pliable at room temperature. As such, it preferably may be stretched, bent, flexed, rolled, twisted, or similarly physically manipulated without being easily damaged and after such activities will generally maintain its shape in the configuration into which it has been fashioned. Preferably, the template material will maintain such properties even after repeated manipulation. Additionally, the material is preferably non-allergenic because of its use against the surface of the skin. The material may be cleaned, disinfected, or sterilized between uses by art recognized methods such as, but not limited to, the use of detergents, alcohol, or autoclaving. Thus in one embodiment the material preferably withstands repeated cleansing, disinfection, sterilization, or any combination thereof without significant deterioration. Still further, the material's physical properties are such that it is sufficiently firm, strong, rigid, etc., to allow the template to function (i.e., after having been manipulated into shape, it tends not to further deform when subjected to the generally lesser forces associated with tracing the shape of a pattern on the surface of a breast). The material is preferably stretchable or deformable in an elastomeric manner, but alternatively it may be stretchable or deformable in a different manner such as by being viscoelastic or plastic. It is preferable that the material, when at room temperature, will undergo elastomeric deformation when subjected to the forces of manual manipulation appropriate for placing and adjusting the template on a breast. Examples of suitable elastomeric materials include silicone, polytetrafluoroethylene (PTFE), rubber, polyurethane, and other polymers with or without reinforcing materials such as dacron mesh. Excellent results to date have been achieved using silicone.

In view of the foregoing properties, the material allows for the shape of the template, or at least a portion thereof, to be deformed or altered to adjust the shape of the guide portion of the template to assume the desired incision pattern to be marked on the surface of the breast. Additionally, the material allows for the template and guide portion to conform to the curvature or irregular surface of a breast and to accommodate breasts of various sizes and shapes quickly and with the application of force within the ready capabilities of a surgeon and that would not be uncomfortable to a patient. As such, desirable incision patterns may be marked on a breast by placing the template in the desired location and orientation, possibly affixing it either before or after adjustment, adjusting the shape of the template to describe the desired incision pattern, pressing or smoothing of the device over the surface of the breast, and tracing the desired incision pattern on the breast with a marking device such as a marker.

B. Configuration of the Template

Figure 5:
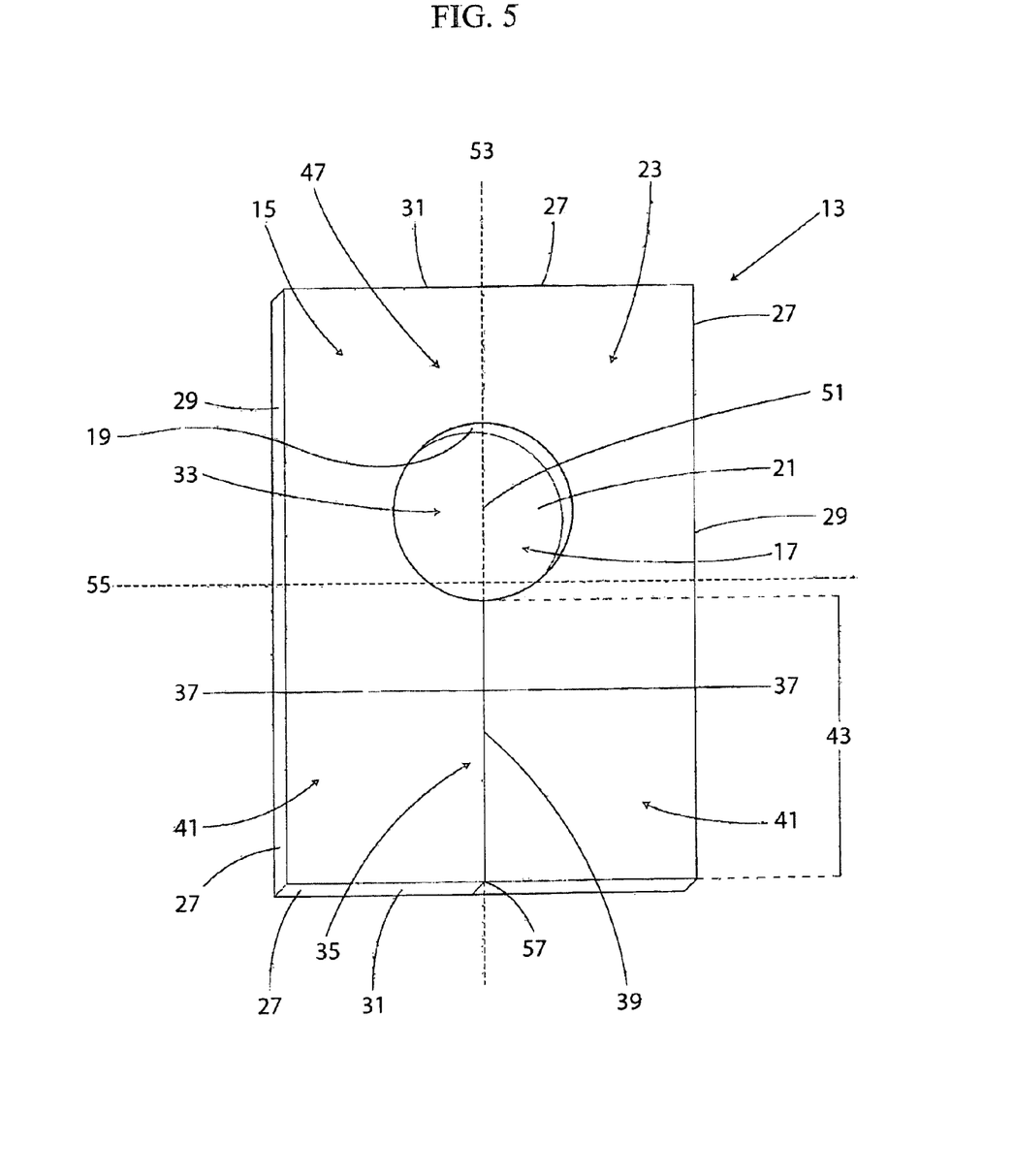
FIG. 5 is a top perspective view of a preferred embodiment of a surgical incision marking template of the invention illustrating the keyhole pattern of the guide portion with the arm portions of the structural portion in a closed position so that the linear pattern of the guide portion forms a slit.
Figure 6:
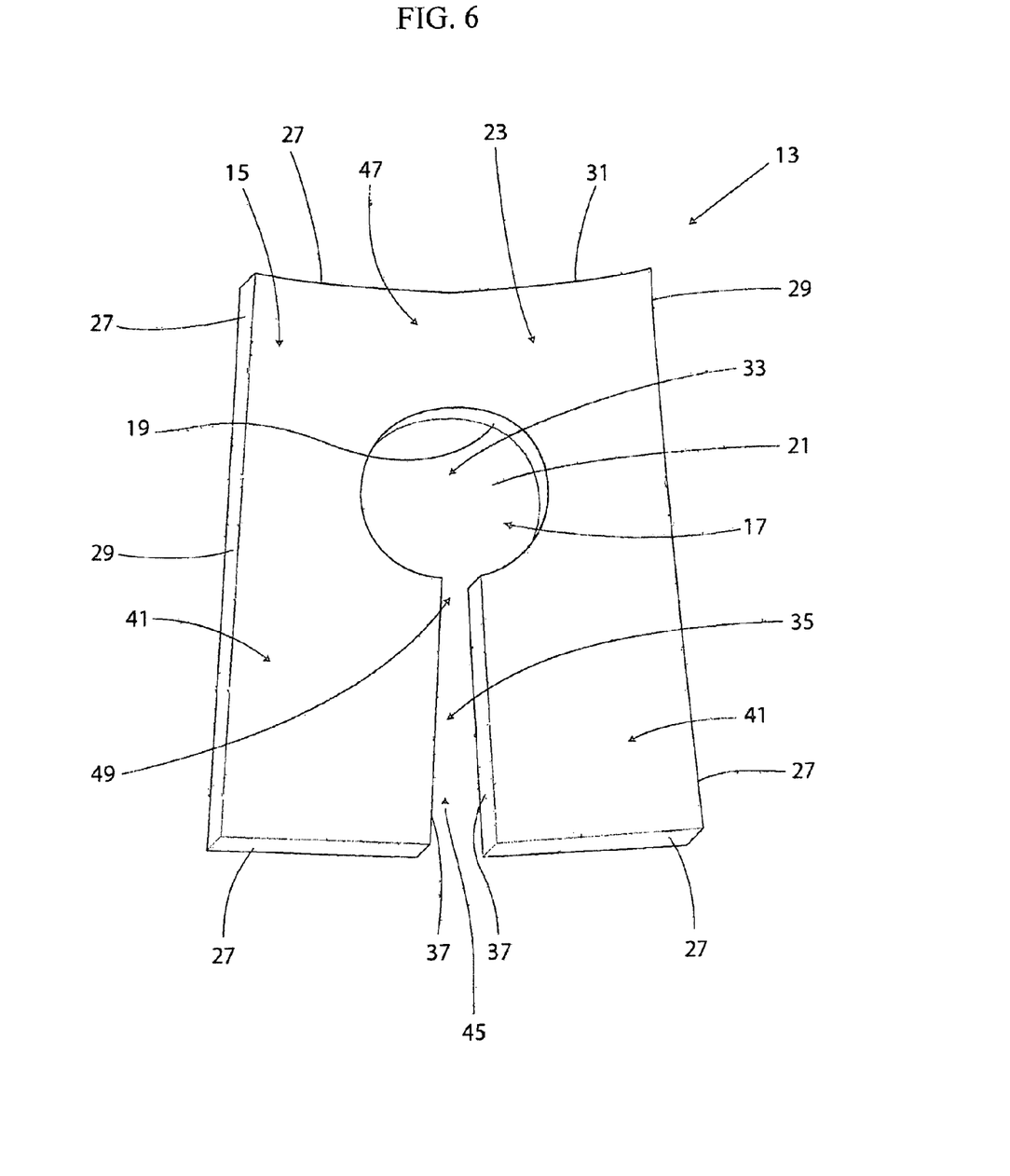
FIG. 6 is a top perspective view of the preferred embodiment of FIG. 5 illustrating the keyhole pattern of the guide portion with the arm portions of the structural portion separated to form an open linear guide pattern.

FIGS. 5 and 6 show a preferred embodiment of the present inventive template device. In general, the template 13 comprises a pliable structural portion 15, which generally surrounds most, if not all, of a guide portion 17; wherein said structural portion or a portion thereof, during use of the template, is contacted with at least some portion of the surface of a breast. As can be seen in FIGS. 5 and 6, the edges of the guide portion 19 are also surfaces or edges of the structural portion, and define an opening or openings 21 within the template that allow for communication through the template to the breast. The edges of the guide portion serve as the guide for marking incision pattern(s) on the breast. The present invention is directed to a template with any guide portion suitable for marking incision patterns. FIGS. 7-10 show non-limiting examples of alternative embodiments. These non-limiting alternative embodiments demonstrate that the configuration of the guide portion is subject to variation, but in each such embodiment it is a configuration that when used as a guide, results in the marking of a breast reduction incision pattern on a breast.

Although the following description is in reference to the preferred embodiment shown in FIGS. 5 and 6, it is largely applicable to the alternative embodiments depicted in FIGS. 7-10 and other possible embodiments of the invention. The template 13 of the present invention comprises a pliable structural portion 15 and a guide portion 17. The structural portion may be entirely solid (as depicted) or it may comprise openings such as holes, perforations, pores, slots, etc. (not shown) but, if present, such openings are not considered to be part of the guide portion. Additionally, the surfaces of the structural portion may be smooth, relatively smooth, or they may be textured, for instance, to prevent the template from slipping once positioned against the skin of the breast. It is to be noted that in the preferred embodiment shown, the template is a single piece, but in alternative embodiments it may be formed of two or more pieces.

i. Structural Portion

As shown in FIGS. 5 and 6, the general shape of the structural portion is that of a sheet of material. By sheet, it is meant that the depth or thickness of the structural portion is small relative to its length and width. It therefore has two opposite large surfaces, a top surface 23 and an opposite bottom surface (not shown), and a shape defined by an outside perimeter edge 27. The structural portion of the template is preferably of a size large enough to cover an area of a breast sufficient to encompass a desired incision pattern which corresponds to the size of the guide portion. The overall template is preferably not so large as to cause it to be unwieldy during use. Additionally, the thickness of the structural portion is not overly critical but is preferably thick enough (depending on the properties of the material) to withstand the handling associated with accurately marking a breast and multiple uses. Further, it is preferably thin enough (depending on the properties of the material) to conform to the surface of a breast and not interfere with marking the incision pattern(s) on the breast. Experiments to date indicate that for a silicone template, the thickness is preferably no less than about 2 millimeters and no more than about 7.5 millimeters.

As set forth in the figures, preferred embodiments of the template are generally rectagonal in shape. Notwithstanding the depicted embodiments, the general shape of the template may be any shape such as a square, triangle, oval, circle, etc. The primary purpose of the structural portion of the template is to embody a guide portion. For example, in rectangular embodiments, the longer sides 29 are typically at least about 11 centimeters and no greater than about 15 centimeters and the shorter of the sides 31 are typically at least about 7 centimeters and no greater than about 9 centimeters. One of skill in the art will recognize that these lengths are non-limiting and serve to give an approximate idea of the dimensions of the device. Experimental results to date indicate that the preferred length and width (for a generally rectagonal device) are about 11 centimeters and about 7 centimeters, respectively. The shape of the structural portion need not be an exact geometric shape nor have straight lines, perfect right angles, precise lengths, etc., as long as it surrounds most, if not all, of a guide portion.

ii. Guide Portion Comprising a Keyhole Pattern

The guide portion comprises the features that provide the edges that serve as the guide for marking the incision pattern on a breast. In the embodiments pictured in FIGS. 5-10, the guide portion 17 comprises an opening or openings 21 extending through the plane of the structural portion (i.e., extending in the direction of one large surface to the other) that allow communication of a marking device through the template to the surface of a breast. The opening(s) 21 are defined by edges of the structural portion 15 that surround the opening(s) 21. These edges are concurrently edges of the guide portion 19 that serve as the guiding edge or surface for marking the incision pattern on a breast. The edges or surfaces are preferably perpendicular, or thereabout, to the plane of the structural portion, but they may be at a different angle as a surgeon may prefer or which might work better with the instrument used to mark the incision pattern. For example, it may be desirable to create an opening such that the size of the opening at the large surface that will be in contact with the breast is smaller than the size of the opening at the opposite large surface. The one or more openings are of a width or size that is, or can be adjusted to be, large enough to allow the marking device to be passed through the opening to contact the surface of the breast.

Figure 7:
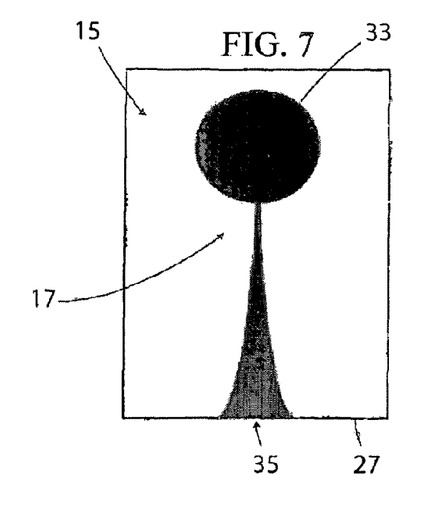
FIG. 7 is a top plan view drawing of an alternate embodiment of a template of the invention with the a slight curvature to the linear pattern of the guide portion.

As shown in the preferred embodiment of FIGS. 5 and 6, the guide portion is configured to comprise at least one generally circular pattern 33 and at least one generally linear pattern 35, such generally linear pattern 35 extending away from the area of the generally circular pattern 33 and towards a perimeter edge 27 of the structural portion 15. In combination, the circular pattern 33 and the linear pattern 35 comprise what is referred to herein as the "keyhole" pattern. Therefore, the guide portion 17 comprises a keyhole pattern. As can been seen in FIGS. 5 and 6, the linear pattern 35 portion of the keyhole pattern can be of various widths or angles. It should be noted that the "linear" pattern is referred to as such not because of the overall shape of the opening it forms (because this shape may be altered as discussed below), but because of the generally linear edges that define this portion of the keyhole pattern. FIG. 7 shows an alternate embodiment in which the "linear" pattern 35 has a curvature to it, but it still extends away from the circular pattern 33 and towards the perimeter edge 27 of the structural portion 15 consistent with the linear pattern 35 of the preferred embodiment shown in FIGS. 5 and 6. Thus the present invention contemplates any generally linear pattern in conjunction with a generally circular pattern that comprises a keyhole pattern consistent with exemplary embodiments depicted. As shown in FIGS. 1 and 3, the incision patterns (dashed lines 1 and 5 respectively) of the short scar technique and the inferior pedicle technique respectively, both include a generally circular pattern 33 and generally linear pattern 35 that correspond to the keyhole pattern of the invention.

Figure 9:
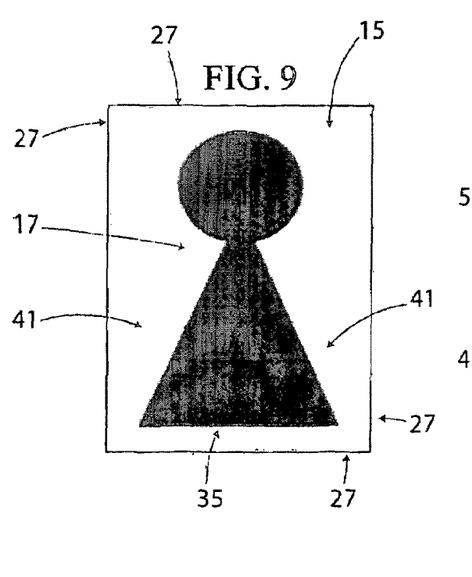
FIG. 9 is a top plan view drawing of an alternate embodiment of a template of the invention with an open linear pattern of the guide portion wherein the linear pattern does not intersect with the outside perimeter edge of the structural portion so that the arm portions may not be easily separated.
Figure 10:
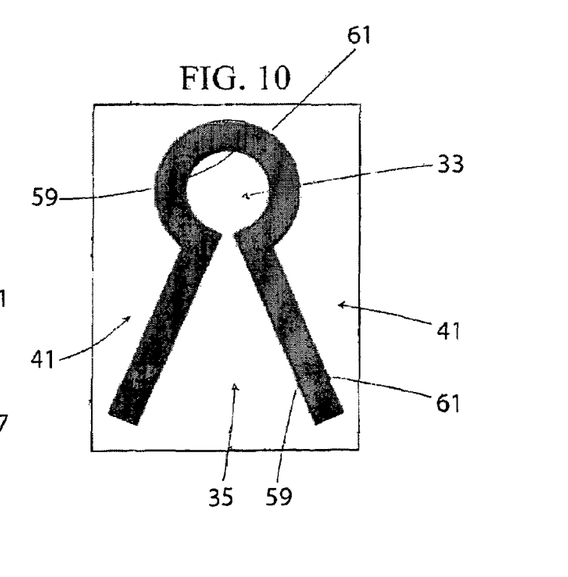
FIG. 10 is a top plan view drawing of an alternate embodiment of a template of the invention comprising parallel edges that form an inner and outer guide portion of different sizes.

In the preferred embodiment of FIGS. 5 and 6, the linear pattern 35 has two opposite edges 37 (shown in FIG. 6) that intersect with the single edge of the circular pattern 33. The edges of the linear pattern likewise intersect with the outer perimeter edge 27 of the structural portion 15 of the template 13. Thus the edge of the circular pattern, the edges of the linear pattern, and the outer perimeter edge of the structural portion preferably form a continuous and uninterrupted edge. In alternative embodiments, the edges of the linear pattern may not intersect with the edge of the circular pattern (not shown), or they may not intersect with the outer perimeter edge of the structural portion as shown in FIGS. 9 and 10. FIG. 5 shows a template wherein the linear pattern is a slit 39 extending from the edge of the circular pattern 33 to the outer perimeter edge 27. The slit separates the area of the structural portion 15 through which it runs into two separate "arm" portions 41. The length of the arm portions 41 preferably provides for a linear pattern 35 with edges of sufficient length to mark the breast from the circular pattern 33 inferiorly (downward) toward the inframammary crease. Typically, the length of the arm portion 43 (measured generally as shown in FIG. 5 as the length of an edge of the linear pattern from its point of intersection with the outer perimeter edge to its point of intersection with the edge circular pattern) is at least about 4 centimeters and no greater than about 10 centimeters. Results to date indicate the length is preferably at least about 5 centimeters and no greater than about 8 centimeters. Most preferably the length is about 5 centimeters. It should be noted that these dimensions, in addition to other dimensions described herein, may be adjusted to some extent by the stretching or pulling of a template comprising certain pliable and stretchable materials. Thus, for example, a template with an unstretched arm portion length of 5 centimeters, could be stretched somewhat such that the arm portion length is greater than 5 centimeters.

FIG. 6 shows the template of FIG. 5 wherein the arm portions 41 have been separated by about 10 degrees along the plane of the sheet (angle measured at an imaginary point where the edges of the linear pattern would meet if extended into the circular opening). Thus, the linear pattern slit 39 of FIG. 5 has been altered into a wider opening 45. In essence, when the arm portions 41 are together in a closed position as shown in FIG. 5, the angle between them is about zero degrees, meaning that they are substantially parallel. Because of the pliable or flexible nature of the template material, this angle can be increased by manual manipulation without breaking, ripping, or tearing the template, the result of which is shown in FIG. 6. As shown in the alternate embodiment of FIG. 8, the guide portion 17 can be configured so that the edges of the linear pattern are at an angle greater than about zero degrees even when the arm portions 41 are not pulled apart from each other. Thus, an even greater amount of separation between the arm portions can be achieved with a lesser amount of flexing or bending of the structural portion. Although not depicted as such, a corresponding alteration in the shape of the circular pattern 33 may be desired to compensate for the increased angle so that the post surgery shape of the areola will result in a perfect or at least near perfect circle.

As noted above, the generally linear pattern remains a linear pattern despite this change in shape because the edges of this portion of the guide portion remain generally linear. As can be seen in FIG. 6, the area of the structural portion 15 opposite of where the generally linear pattern 35 intersects the generally circular pattern 33 remains substantially unchanged. This general area 47 acts as a hinge, in conjunction with the pliable or flexible nature of the template material, to allow separation of the arm portions along the plane of the template and their independent positioning. The angle and area of separation between the arm portions can be altered according to the desired incision pattern to be marked. For instance, if a narrower incision area is desired, the arm portions will not be as widely separated when the template is placed on the breast as when a wider incision area is desired. The maximum angle between the arm portions may be limited by the pliability of the material used, but experiments to date suggest that an angle of up to about 80 degrees is sufficient for use in breast reduction surgery. Such angle is readily achievable using silicone as the template material. In general, an angle of about 45 degrees to about 70 degrees of separation between the arm portions is desirable for creating the desired keyhole pattern for breast reduction surgery. In cases of breast reduction and areolar/nipple relocation, it is generally preferable that the edges of the linear pattern substantially span i.e., fall to either side of the areola (as illustrated in FIGS. 1 and 3) such that the incision pattern does not substantially extend through the areola.

Because of the pliable or flexible nature of the template material, the arm portions 41 may also bend, flex, curve, etc., above and below the plane of the template and independent of the separation between the two arms. This feature of the current invention is especially advantageous over known template devices consisting of wire. Unlike previous wire templates, the flexibility of the current invention allows the template to easily conform to the curvature and variations of shape, size and irregularity of breasts. Such conformation is achievable, and depending on the flexibility of the material, may simply occur by positioning the template on a breast. For example, the template may drape over the breast and assume the shape of the breast simply through the pull of gravity. Manual manipulation such as smoothing, pulling, stretching, shaping and the like may further be desired to achieve optimum conformation. Such close conformation of the template to the shape of the breast is desirable in maintaining contact between the template and the surface of the breast.

As shown in the preferred embodiment of FIG. 5, the generally circular pattern 33 of the guide portion 17 is a perfect or near perfect circle when the arm portions 41 of the structural portion 15 are together in a closed position. Such perfect or near perfect circular shape corresponds to the generally ideal shape of an areola. However, in alternate embodiments, the generally circular pattern may vary therefrom, for example it may be ovalized (symmetrically or asymmetrically). Depending on the material of the template, the shape of the circular opening may be modified by removing materials (e.g., by using scissors, a knife, or other device) to further adapt the template to a desired application.

As shown in FIG. 6, when the arm portions 41 are separated, a gap 49 may be formed in the edge of the generally circular pattern 33, corresponding to a change in the shape of the circular pattern. The further apart the arm portions 41 are separated, the larger the alteration of the shape of the circular pattern 33. Thus, when the template is placed on a breast, the arm portions separated, and the incision pattern marked using the circular and linear patterns of the guide portion as guides, the resulting circular incision pattern will not necessarily be the perfect or near perfect circle of the desired post-operative areolar shape. However, just as when the arm portions of the template are closed together reforming the original circle, when the skin is pulled together following removal of the portion of skin between the marks of the linear pattern, the resulting post-operative shape of the areola will be the desired circular shape.

The diameter of the generally circular pattern (measured at the edge(s) or surface(s) used to make the markings) is preferably about the desired post-operative size or diameter of the areola. Typically, the diameter is at least about 30 millimeters and no greater than about 50 millimeters. Experimental results to date indicate the size or diameter is preferably at least about 38 millimeters and no greater than about 42 millimeters. In certain embodiments, such as depicted in FIG. 10, there may be two sets of edge(s) or surface(s) that allow for forming two circular patterns with distinct sizes or diameters or ranges thereof in the case of a stretchable template. Although not depicted in a figure, it is contemplated that more than two nested patterns may be formed in the template.

The position of the generally circular pattern 33 within the template may 13 be varied but it is preferably located somewhat off-center of either the x or y axis of the template (i.e., x is length and y is width or vice versa, but neither x or y is depth), and centered along the other axis. As shown in FIG. 5, for example, in a rectangular embodiment the center 51 of the generally circular pattern 33 is typically near the center line 53 of the shorter sides 31 and away from the center line 55 of the longer sides 29. Stated another way, it will be approximately centered between the two longer sides and closer to one of the shorter sides than the other. In such a preferred configuration, the linear pattern 35 will generally extend from the circular pattern 33 to the outer edge of the short side furthest away from the center of the circular pattern 33. This preferred configuration accommodates arm portions 41 of sufficient length without an excess of material extending opposite of the linear pattern. The point 57 at the outside perimeter edge 27 of a side of the structural portion to which the generally linear pattern is directed is preferably about equidistant there along, however it need not be.

Figure 8:
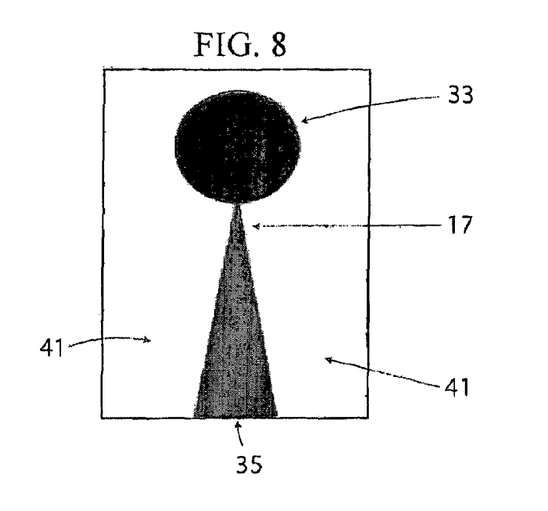
FIG. 8 is a top plan view drawing of an alternate embodiment of a template of the invention with an open linear pattern of the guide portion without deflection of the arm portions.

FIGS. 8-10 illustrate examples of alternative embodiments of the present invention. For example, in FIG. 8, the linear pattern 35 of the guide portion 17 forms a wider slit. Thus, a wider width of the linear pattern is achievable with less flexing of the arm portions 41 away from each other as compared to the embodiment of FIGS. 5 and 6. In FIG. 9, the linear pattern 35 is similarly wide as in FIG. 8. Because the linear pattern does not however intersect with the outer perimeter edge 27 of the structural portion 15, the arm portions 41 are not free to move independently, although the overall template retains its pliable and flexible nature to conform to the breast. Thus, in this embodiment, adjustability of the angle and size of the linear pattern would be limited as compared to the embodiments shown in FIGS. 5-8. In some applications however, a fixed shape may be preferable to an adjustable one. For example, independent positioning of the arm portions could possibly result in asymmetrical positioning. Likewise, the alternative embodiment depicted in FIG. 10 would also lack independent movement of the arm portions 41. However, as is shown, the guide portion 17 has two edges that run parallel to one another 59 and 61 which creates a circular pattern 33 with concentric or nested circles, and a linear pattern 35 with an outer and an inner edge. Thus, depending on which edge is used as a guide, the size of both the linear pattern and the size of the circular pattern may be varied. One skilled in the art will recognize that numerous variations to the shape of the guide portion keyhole pattern may be devised without straying from the scope or concept of the current invention.

C. Method of Utilizing a Pliable Marking Template

The present invention relates to a method for marking a breast with an incision pattern for breast reduction and mastopexy surgery using the pliable template of the invention. Prior to marking the breast, the pliable template is placed on the breast. The template is preferably placed on the breast while the patient is a standing or sitting position. More preferably, the template is placed on the breast while the patient is standing and the breast is hanging naturally. The top edge of the circular pattern of the guide portion of the template is used to mark the area of the incision pattern that represents the post operative position of the top edge of the areola. Therefore, it is preferable that top edge of the circular pattern of the template be placed so that it coincides with the desired post operative location of the top edge of the areola. To ensure that the positions of the areolas of each breast of a patient are symmetrical or nearly symmetrical when both breast are operated on, a desired distance is measured from the suprasternal notch to the top or about the top of the desired new position of the areola. The location of the top or about the top of the desired new position of the areola will be used to determine the positioning of the template on the patient. Although perfect symmetry may not be achievable, this step is helpful in achieving desirable results. One skilled in the art will realize that the distance to the top or about the top of the desired new position of the areola will be determined by the experience of the surgeon under the circumstances of the surgery and the physical characteristics of the particular patient.

Once the position is determined, the orientation and shape of the template is adjusted such that the shape of the guide portion on the breast is of a pattern corresponding to the desired incision pattern and preferably a keyhole incision pattern. In general, for both the vertical short scar technique and the inferior pedicle technique, the linear pattern of the guide portion extends inferiorly (i.e., downward) from the circular pattern and towards the inframammary crease. The angle of the opening between the arm portions of the structural portion may be varied such that the linear pattern on the breast is of the desired width. This width may be determined by factors such as for example, but not limited to, how much skin is to be resected during the surgery. Due to the pliable nature of the template material, the template may be further smoothed, pressed, or otherwise formed to the curvature and shape of the breast so that it conforms thereto. The template may also be secured to the breast at any time to maintain its position. Means of securing the template include any recognized method such as taping, tacking, gluing, etc. Preferably, the template is taped in place.

Once in place, one or more surfaces or edges of the guide portion of the template, in particular the generally circular pattern and the generally linear pattern of the keyhole pattern, are used to trace the incision pattern on a breast. Any number of art recognized marking devices may be used and in a preferred method the marking device is a permanent marker such as a Sharpie® pen or marker.

The invention has been illustrated through the disclosure contained in the figures and detailed description of the preferred embodiments. This disclosure is merely intended to be exemplary of the invention and there are alternatives that would be apparent to those of skill in the art upon reading this disclosure. Any alternatives or modifications are included as part of the invention which is intended to be limited solely by the scope of the claims appended hereto and their legal equivalents.

What is claimed:

1. A surgical incision marking template for marking a breast with an intended incision pattern prior to surgery, said template comprising a pliable structural portion comprising a guide portion, said guide portion being substantially shaped into a keyhole pattern, wherein said pliable structural portion is made at least in part from a material of one or more of silicone, rubber, PTFE, or other elastomer, and wherein the pliable structural portion also comprises a Dacron mesh reinforcing material.

2. The template of claim 1 wherein said structural portion is sufficiently large to accommodate the guide portion.

3. The template of claim 1, wherein the structural portion has a top surface and a bottom surface, and wherein said top surface, said bottom surface, or both top and bottom surfaces are textured to prevent slipping of the template against the skin of a patient.

4. The template of claim 1 wherein the keyhole pattern is defined by an edge in the template and comprises a generally circular pattern and a generally linear pattern.

5. The template of claim 4 wherein said guide portion is generally centered along at least one axis of said structural portion, and wherein the generally linear pattern extends generally away from the generally circular pattern to an outer edge of said structural portion.

6. The template of claim 5 wherein the generally linear pattern divides a portion of the structural portion into arm portions that are independently positionable.

7. The template of claim 6 wherein either of said arm portions can be angled with respect to the other of said arm portions to thereby create a variation in the shape of the keyhole pattern.

8. The template of claim 1 wherein said keyhole pattern is defined by a continuous edge extending inwardly from an outer edge of the pliable structural portion.

9. The template of claim 8 wherein said pliable structural portion has a width, said edge extending through said width and being angled there along.

10. The template of claim 1 wherein said keyhole pattern is formed from a plurality of edges.

11. The template of claim 10 wherein at least one of said plurality of edges forms a generally circular pattern and another of said plurality of edges forms a generally linear pattern.

12. The template of claim 10 wherein one continuous edge forms a first keyhole pattern and a second continuous edge forms a second keyhole pattern.

13. A method for marking a breast with an incision pattern for breast reduction surgery, the method comprising:
 a) placing the template device of claim 1 on a breast such that the top edge of a circular pattern of the guide portion is at or near the level of the desired post-surgery position of the top edge of the areola;
 b) adjusting the orientation and shape of the structural portion such that the shape of the guide portion on the breast is of a keyhole pattern corresponding to the desired incision pattern; and
 c) tracing along one more or edges of the guide portion with a marking instrument to mark the incision pattern on the breast.

14. The method of claim 13 further comprising securing the template to the breast in the desired position.

15. The method of claim 13 wherein tracing includes marking along substantially the entirety of the keyhole pattern.

16. The method of claim 13 further comprising measuring a distance from a suprasternal notch of a patient to a location at or about the desired post-surgery position of the top edge of the areola, wherein said location is used to determine the positioning of the template device.

17. The method of claim 16 wherein surgery is performed on both of the patient's breasts, and the distance from the suprasternal notch to a location on each breast is calculated to ensure that the post-surgery position of the areolas is symmetrical, near symmetrical, or as near symmetrical as is reasonably achievable.

* * * * *